US006191316B1

(12) United States Patent
Fennhoff et al.

(10) Patent No.: US 6,191,316 B1
(45) Date of Patent: Feb. 20, 2001

(54) METHOD FOR PROCESSING MOTHER LIQUORS FROM THE PRODUCTION OF BISPHENOL

(75) Inventors: Gerhard Fennhoff, Willich; Hans-Josef Buysch; Gerd Fengler, both of Krefeld, all of (DE)

(73) Assignee: Bayer Aktiengesellschaft, Leverkusen (DE)

(*) Notice: Under 35 U.S.C. 154(b), the term of this patent shall be extended for 0 days.

(21) Appl. No.: 09/423,764

(22) PCT Filed: May 5, 1998

(86) PCT No.: PCT/EP98/02642

§ 371 Date: Nov. 12, 1999

§ 102(e) Date: Nov. 12, 1999

(87) PCT Pub. No.: WO98/52897

PCT Pub. Date: Nov. 26, 1998

(30) Foreign Application Priority Data

May 16, 1997 (DE) .............................................. 197 20 540

(51) Int. Cl.[7] .................................................. C07C 39/12
(52) U.S. Cl. ............................................ 568/728; 568/727
(58) Field of Search .................................... 568/728, 727, 568/749

(56) References Cited

U.S. PATENT DOCUMENTS

| 2,497,503 | 2/1950 | Jones .................................. 260/621 |
| 2,775,620 | 12/1956 | Williamson ........................ 260/619 |
| 3,242,219 | 3/1966 | Farnham et al. .................... 260/619 |
| 3,466,337 | 9/1969 | Smith et al. ........................ 260/621 |
| 4,277,628 | 7/1981 | Carnahan ............................ 568/749 |
| 4,308,405 | 12/1981 | Kwantes ............................. 568/727 |
| 4,594,459 | 6/1986 | Inoue .................................. 568/781 |
| 4,859,803 | 8/1989 | Shaw .................................. 568/727 |
| 4,876,391 | 10/1989 | Kissinger ........................... 568/724 |
| 4,906,789 | 3/1990 | Grzywa et al. .................... 568/727 |
| 4,935,553 | * 6/1990 | Iimuro ............................... 568/727 |
| 5,198,591 | * 3/1993 | Kiedik ............................... 568/727 |
| 5,300,702 | 4/1994 | Perkins et al. ..................... 568/724 |
| 5,315,042 | 5/1994 | Cipullo et al. ..................... 568/727 |
| 5,430,199 | * 7/1995 | Caruso ............................... 568/724 |
| 5,504,251 | * 4/1996 | Dyckman .......................... 568/754 |
| 5,672,774 | * 9/1997 | Dyckman .......................... 568/749 |
| 5,783,733 | * 7/1998 | Kissinger ........................... 568/724 |
| 6,025,530 | * 2/2000 | Dyckman .......................... 568/754 |

FOREIGN PATENT DOCUMENTS

| 0 017 852 | 10/1983 | (EP) . |
| 0 332 033 | 9/1989 | (EP) . |
| 0 552 518 | 9/1995 | (EP) . |
| 0 630 878 | 3/1998 | (EP) . |

OTHER PUBLICATIONS

Ullmann's Encyclopedia of Industrial Chemistry, 5th edition, vol. A19, (1993).

Editiors, B. Elvers, S. Hawkins, G. Schulz, Phenol Derivatives, pp. 348–352.

Ullmann's Encyclopedia of Industrial Chemistry 5th edition, vol. B4, (1993).

Reaction Columns, Otto Wörz, Hans–Horst Mayer, pp. 321–328.

* cited by examiner

*Primary Examiner*—Michael L. Shippen
(74) *Attorney, Agent, or Firm*—Joseph C. Gil; Aron Preis

(57) ABSTRACT

The present invention relates to a process for working up the residual mother liquors from the production of dihydroxydiarylalkanes (bisphenols) discharged from the process once the bisphenol has been separated.

1 Claim, No Drawings

METHOD FOR PROCESSING MOTHER LIQUORS FROM THE PRODUCTION OF BISPHENOL

The present invention relates to a process for working up the residual mother liquors from the production of dihydroxydiarylalkanes (bisphenols) discharged from the process once the bisphenol has been separated.

The production of bisphenols by the acid-catalysed reaction of ketones with phenol is known. There have been a number of different proposals for this (cf, for example, U.S. Pat. No. 2,775,620, EP-A 342 758, EP-A 616 993, EP-A 342 758, DE-OS 3,833,900, U.S. Pat. No. 4,308,404, U.S. Pat. No. 4,308,405, EP-A 630 878, U.S. Pat. No. 4,876,391, U.S. Pat. No. 3,242,219).

There is a survey of the older literature on bisphenol production in Ullmann's Encyclopedia of Indust. Chem., 5th. Edition, Vol. A 19, pages 348–52. As a rule bisphenols, especially bisphenol A (BPA), industrially the most important of the bisphenols, are prepared by introducing ketone and phenol into a recirculated mother liquor obtained from the working up of bisphenol, this mixture is passed through acidic ion exchangers and the conversion to bisphenol takes place. Any ketone which may possibly not have reacted is recovered from the reaction mixture and led back into the reaction. The reaction mixture is cooled, the bisphenol is if necessary allowed to crystallise out as phenol adduct, separated off and washed with phenol. The phenol is separated from the adduct by flash distillation and pure bisphenol is recovered. The mother liquor from the crystallisation is passed through acidic ion exchangers and isomers contained therein undergo rearrangement to form bisphenol. The bisphenol thus formed is separated by crystallisation and the crystallisate obtained is passed to the first crystallisation step. A portion (approximately 10 to 20%) of the mother liquor now obtained is set aside; the bulk is returned to the reaction. Phenol is distilled off from the portion set aside and is returned to the reaction. The residue obtained during the distillation is removed from the process and is used, for example, for the preparation of phenol resin.

An appreciable quantity of valuable compounds, such as bisphenol and isomers, are lost in the portion which is set aside and ultimately discharged. This removal from the mother liquor is absolutely essential, so as not to allow the quantity of unusable and interfering compounds to become too great. Attempts have therefore been made to work up and to decompose the discharged portion, in order to recover the valuable materials for use in the production of bisphenol. For this, too, there have been a number of different proposals.

By pyrolysis at about 300° C. it is possible to obtain moderate yields of phenol and alkylphenols, which have still to be thoroughly purified (U.S. Pat. No. 2,497,503). A hydrogenation treatment also leads to valuable products, as is disclosed in EP-A 17 852. The decomposition can also be accelerated by acidic and basic compounds. However, only phenol is obtained by using acids such as sulphuric acid or toluenesulphonic acid (U.S. Pat. No. 3,466,337). Basic catalysts, on the other hand, effect a decomposition of the discharged materials into phenol and isoalkenylphenol. Catalysts mentioned are alkali metal compounds, such as NaOH, KOH, $NaHCO_3$, Na acetate, Na hypophosphite, $K_2CO_3$, MgO and Al isopropylate (U.S. Pat. No. 4,277,628, U.S. Pat. No. 4,594,459, U.S. Pat. No. 4,131,749).

In this procedure, however, only a part of the discharged material is decomposed, and operation is intermittent or semicontinuous. Wholly continuous processes are unknown.

These processes have been improved, as regards a higher purity of the bisphenol, in that the phenol/isoalkenylphenol mixture from the decomposition is introduced into the first mother liquor after the separation of the first bisphenol portion. The mixture is passed over the acid catalyst and the reaction of isoalkenylphenol with phenol and the rearrangement are allowed to proceed simultaneously. The second bisphenol portion is then separated from the mixture by crystallisation and the second mother liquor is again removed for decomposition. The second bisphenol portion is introduced into the first crystallisation. The purity of the bisphenol is thereby somewhat increased, but the process is rendered more complicated by an additional circulation (U.S. Pat. No. 4,954,661).

It has also been proposed that the second mother liquor in the bisphenol process described above, or the first mother liquor after separation of the first quantity of bisphenol and after the rearrangement, be at least partly worked up by distillation, in order better to utilise the valuable products contained therein. The bisphenol thus obtained is reintroduced into the first crystallisation step and purified there. The low-boiling components containing isomers are introduced into the reaction (WO 94/20445 and EP-A 552 518). The difficulty lies in obtaining at justifiable expense from the mother liquor, which is highly enriched by isomers and by-products, sufficiently pure fractions particularly low in chromans and indans, which are difficult to remove, without excessively increasing the no longer usable residue and diminishing the yield. Because of this, a portion of the distillation products have to be discarded.

The fractions low in bisphenol which are obtained during the distillation may also be decomposed and the decomposition products reintroduced into the process (EP-A 332 203).

It has now been found that the yield from bisphenol synthesis using the above-described process may simply be increased by mixing the discharged portion of the second mother liquor, once the phenol has been removed by distillation, with a basic catalyst and continuously apportioning it as a melt into a reactive rectification stage. During the reactive rectification, this melt is decomposed into a mixture of phenol and isoalkylphenol, obtained as an overhead product, which flows into the reaction, and bottoms which, once acidified, are apportioned into a second reactive rectification stage, where they are decomposed into phenol which, optionally after further purification, is returned to the reaction, and second bottoms which are discarded.

Suitable aromatic hydroxyl compounds for the production of the educts for the process according to the invention are not substituted in the para position and contain no substituents of the second order, such as cyano groups, carboxyl groups or nitro groups; examples which may be mentioned are phenol. o- and m-cresol, 2.6-dimethylphenol, o-tert.-butylphenol, 2-methyl-6-tert.-butylphenol, o-cyclohexylphenol, o-phenylphenol, o-isopropylphenol, 2-methyl-6-cyclopentylphenol o- and m-chlorophenol, 2,3, 6-trimethylphenol. Preferred compounds are phenol, o- and m-cresol, 2,6-dimethylphenol, o-tert.-butylphenol and o-phenylphenol; phenol is particularly preferred.

Suitable ketones contain at least one aliphatic group on the carbonyl function: examples which may be mentioned are acetone, methyl ethyl ketone, methyl propyl ketone. methyl isopropyl ketone, diethyl ketone, acetophenone, cyclohexanone, cyclopentanone, methyl-, dimethyl- and trimethylcyclohexanonc, which may also have germinal methyl groups, such as 3,3-dimethyl-5-methylcyclohexanone (hydroisophorone). Preferred compounds are acetone, acetophenone, cyclohexanone and its homologues containing methyl groups: acetone is particularly preferred.

Educts for the process according to the invention are the mother liquors arising during the production of dihydroxy-diarylalkanes by the reaction of aromatic hydroxy compounds with ketones and isoalkenylphenols on acid catalysts.

Preferred educts for the process according to the invention are in particular also the mother liquors remaining after separation of the bis(4-hydroxyaryl)alkanes, which, after addition of the consumed hydroxy compounds and optionally removal of a certain proportion in order to avoid the accumulation of unwanted by-products, are returned to the process: in the case of bisphenol A synthesis, such mother liquors contain approx. 78–88 wt. % of phenol and 22–12 wt. % of bisphenol A and by-products of the following composition:

| bisphenol A | 40–65 wt. % |
|---|---|
| o,p-bisphenol | 14–19 wt. % |
| trisphenol | 2–6 wt. % |
| chromans | 4–17 wt. % |
| 1,3,3-trimethyldihydroxyphenylindans | 3–13 wt. % |
| further secondary products | 3–15 wt. % |

Suitable catalysts for the basic decomposition are those mentioned in the literature, preferably alkali metal oxides and hydroxides, particularly preferably NaOH and KOH. In the process according to the invention, they are introduced into the melt of the decomposition educts, dissolved and homogeneously distributed, the temperature expediently being between 100° C. and 200° C., preferably 120° C. and 180° C.

Suitable catalysts for the acid decomposition are those mentioned in the literature, preferably sulphuric acid, phosphoric acid, phosphorous acid, the partial salts thereof, such as $NH_4HSO_4$, $NaHSO_4$, $KHSO_4$, $NaH_2PO_4$, $KH_2PO_4$, $NH_4H_2PO_4$, $NH_4H_2PO_3$, $KH_2PO_3$ and analogues, also the organic derivatives of these acids, namely aromatic sulphonic acids and disulphonic acids, such as benzenesulphonic acid, toluenesulphonic acid, xylenesulphonic acid, phenolsulphonic acid, diphenyldisulphonic acid, diphenyl ether disulphonic acid, then aromatic phosphonic and phosphinic acids, such as benzene-, toluene- xylenephosphonic and -phosphinic acids, diphenyldiphosphonic acid and diphenyldiphosphinic acid, also solid acids, such as acidic aluminium oxides, aluminas such as bentonites and montmorillonites, zeolites, titanium oxide and zirconium oxide, niobium oxide and tantalum oxide; acidic aluminas are preferred.

The quantities of catalysts added to the mixture to be decomposed are from 0.01 wt. % to 5 wt. %, preferably from 0.05 to 3 wt. %, particularly preferably from 0.1 to 2 wt. %, based on the quantity of decomposed mixture.

To render adherence to these specified quantities possible in the case of acid catalysts, after the basic decomposition the basic catalysts must either be removed from the bottoms, which in any event would probably be too expensive, or they must first be neutralised by a strong acid, before the addition of the required quantity of acid catalyst takes place. In this way the presence of sufficient quantities of active acid is ensured. For the purpose of the invention, acidification therefore means that acid is added to the bottoms from the basic decomposition in a quantity such that both the basic catalyst contained therein is neutralised and over and above this there is available a sufficient quantity of acid catalyst for the subsequent acidic decomposition.

The catalysts, for example, dissolved or suspended in phenol, may be metered continuously into the stream flowing in the column where decomposition takes place. But it is also possible, in intermediate containers, to admix them in batches to the material to be decomposed and then to convey this mixture continuously into the column where decomposition takes place.

The columns in which the reactive rectifications are carried out correspond to the distillation columns generally used. In the columns, the decomposition takes place beneath the separation by distillation and fractionation of the decomposition products phenol and isoalkenylphenol from the undecomposed or perhaps undecomposable compounds. In the course of this the decomposition products, generally already sufficiently pure for further use, leave at the top. The undecomposable constituents are discharged as bottoms. Reactive rectifications are known to the person skilled in the art and are described, for example, in Ullmann's Encyclopedia of Industrial Chemistry, 5th. Edition, Vol. B 4, pages 321–8.

In the present case it may be advantageous to decrease the column diameter appropriately in the lower part of the columns where decomposition takes place, to correspond to the decreasing volume of liquid and gas from top to bottom in the column during the decomposition.

In order to establish a suitable residence time in the column for the material being decomposed, it is useful to insert trays into the columns where decomposition takes place. This applies particularly to the part in which the decomposition proceeds. In the upper part, the use of filler material or packings may be advisable for an effective separation of the products.

In the event that the purity of the phenol distilling off from the second decomposition column is inadequate for use in the bisphenol synthesis, it may be passed into an additional column or else into the first decomposition column and fiuther purified there.

The process according to the invention may particularly advantageously be combined with highly selective bisphenol production processes. These processes are distinguished by the use of the lowest possible ketone concentration and low temperature. This is achieved by reacting phenol and the mother liquor returning to the reaction with ketone and isoalkenylphenol in at least two reactors connected in series which contain acidic ion exchangers and which are operated starting from the lowest possible temperature which, however, rises in the direction of increasing conversion, wherein the total quantity of ketone and isoalkenylphenol is apportioned between the individual reactors and distributed homogeneously in the reaction mixture before the introduction into the respective reactors.

It is useful to provide mixing units of known type in front of the individual reactors, in order to ensure the homogeneous distribution of ketone and isoalkenylphenol in the starting phenol and reaction mixture respectively, as well as heat exchangers for the required tempering of the mixture before the passage through the catalyst bed.

After leaving the reactors, the unreacted ketone is first removed by distillation and the first crystallisation then performed. The crystals are separated and washed with phenol; the bisphenol is then isolated. The mother liquor is then dehydrated and passed through the rearrangement reactor. After rearrangement, a second part of the bisphenol is crystallised from the reaction mixture, separated, washed and introduced into the first crystallisation step. The mother liquor from the second crystallisation step is divided and 80 to 90% are returned to the reaction.

The remaining 10 to 20% are evaporated, the distilled phenol is fed into the reaction or washing. The remaining residue, which contains bisphenol, isomers and secondary products of various types, once mixed with basic catalysts, is metered continuously as a melt into a reactive rectification and therein are decomposed at bottom temperatures of 190° C. to 270° C., preferably at 200° C. to 260° C., particularly preferably at 210° C. to 250° C., and pressures of 15 to 0.5 mbar, preferably 12 to 1 mbar, particularly preferably 10 to 1 mbar. The distillate, consisting of phenol and isoalkenylphenol and its oligomers, is passed to the reaction, the bottoms, after acidification, are metered into a second reactive rectification which is similar to the previous one and therein are decomposed at 150° C. to 260° C., preferably at 160° C. to 250° C., particularly preferably at 170° C. to 240° C. and at the pressures given above. Thereby, phenol is distilled off and may optionally further be purified through a column and mixed into the reaction stream. Bottoms are withdrawn at the foot of the column, and these are removed for disposal.

If the bottom component resulting from the basic decomposition, owing to a relatively small production run in a bisphenol plant, is too small for the economical operation of one column, it is advisable to combine these small quantities from several runs, or to collect the bottoms from one plant to form a larger quantity and then to decompose this in a suitable apparatus.

Using the process according to the invention, it is possible considerably to increase material yields in bisphenol production in a completely continuous, simple operation requiring little elaborate plant and equipment.

EXAMPLE

A resin from conventional bisphenol A production, obtained after separation of BPA, rearrangement, a second BPA separation stage and removal of phenol by distillation, and of the following composition:

0.5% phenol
0.90% dimethylxanthene
0.33% o,o'-bisphenol
17.74% o,p'-bisphenol
6.31% chromans
56.31% BPA
7.05% indans
0.90% spirobisindans
4.37% trisphenol
1.18% trihydroxychromans (MW 402)
4.26% unknown compounds after melting and addition of 0.3 wt. % of KOH, was continuously introduced at a temperature of 145° C. into a 10-plate column having a liquid content (holdup) of 370 ml in a quantity of 400 g/h. The column was enclosed in a heating element adjusted to 180° C., provided at the base with a bottom adjusted to a temperature of 235° C. and, at the top, with a mirrored Vigreux column of a length of 50 cm as the separation apparatus. During operation at 2 mbar, a distillate was continuously discharged from the reactive column via the Vigreux column and a proportion of the apportioned quantity of resin flowed into the bottom flask, from which material was continuously drawn off in a quantity such that it remained approximately half full. After some hours, a distillate of the following composition was obtained 50.4% phenol
0.03% o,o'-bisphenol
0.04% o,p'-bisphenol
0.3% chromans
1.2% dimethylxanthene
1.3% unknown components remainder p-isopropenylphenol and oligomers thereof, which corresponded to approx. 50% of the apportioned quantity of resin and accordingly approx. 50 wt.% of residue from the bottom flask.

A relatively large quantity of this residue was collected, combined with sufficient sulphuric acid to convert the KOH present into $KHSO_4$, and 0.9 wt.% of an acidic phyllosilicate (Tonsil Optimum), relative to the quantity of residue, was also added, the mixture stirred and decomposed in a similar manner to the BPA resin in the apparatus described above, wherein the column was adjusted to ~150° C. and the bottom temperature to 180 to 190° C. 62% of the apportioned quantity of residue passed over continuously as a distillate of the composition 91.5% phenol
0.02% o,o'-bisphenol
0.14% o,p-bisphenol
1.90% chromans
0.01% dimethylxanthene
0.04% BPA
0.17% indan
0.41% spirobisindan
5.8% unknown compounds The residue from this second decomposition was accordingly 38 wt. % of the first residue and 19 wt. % of the originally introduced BPA resin. On the assumption that, depending upon the process, 5000 to 6000 tpy of resin are produced from a BPA output of 100,000 tpy, the quantity of waste may be reduced to 1000 to 1200 tpy by using the process according to the invention and, where the decomposition products are used for BPA synthesis, the yield of BPA may be raised by 4000 to 4800 tpy, corresponding to approx. 4 to 5%.

What is claimed is:

1. In the working up the mother liquor obtained in the process for producing a dihydroxydiarylalkane by reacting phenols with ketone and isoalkenylphenol in the presence of acid catalyst the improvement comprising (a) removing phenol from said mother liquor by distillation, combining the bottoms thus obtained with a basic catalyst and continuously decomposing the combination in a reactive rectification stage into (i) phenol and isoalkenylphenol which pass overhead as the distillate, and (ii) bottoms, and (b) mixing said bottoms with an acid catalyst, continuously introducing the resulting mixture into a second reactive rectification stage to cause the decomposition of the mixture into (i) phenol and (ii) discarded bottoms, and (c) returning the phenol and isoalkenylphenol from stages (a) and (b) to said process.

* * * * *